US008506956B2

(12) United States Patent
Ueda et al.

(10) Patent No.: US 8,506,956 B2
(45) Date of Patent: *Aug. 13, 2013

(54) METHOD FOR STABILIZING REDUCED COENZYME $Q_{10}$

(75) Inventors: Takahiro Ueda, Kobe (JP); Shiro Kitamura, Akashi (JP); Yasuyoshi Ueda, Himeji (JP)

(73) Assignee: Kaneka Corporation, Osaka (JP)

( * ) Notice: Subject to any disclaimer, the term of this patent is extended or adjusted under 35 U.S.C. 154(b) by 627 days.

This patent is subject to a terminal disclaimer.

(21) Appl. No.: 11/586,511

(22) Filed: Oct. 26, 2006

(65) Prior Publication Data

US 2007/0104701 A1 May 10, 2007

(30) Foreign Application Priority Data

Oct. 31, 2005 (JP) ................................ 2005-316298

(51) Int. Cl.
*A61K 38/43* (2006.01)

(52) U.S. Cl.
USPC ........................................ 424/94.1; 424/455

(58) Field of Classification Search
None
See application file for complete search history.

(56) References Cited

U.S. PATENT DOCUMENTS

| | | | | |
|---|---|---|---|---|
| 4,751,241 | A * | 6/1988 | Motoyama et al. | 514/532 |
| 2004/0126367 | A1 * | 7/2004 | Fujii et al. | 424/94.1 |

FOREIGN PATENT DOCUMENTS

| | | | |
|---|---|---|---|
| JP | 10-109933 | | 4/1998 |
| WO | WO 9517953 | A1 * | 7/1995 |
| WO | WO 01/52822 | A1 | 7/2001 |
| WO | WO 03/006408 | A1 | 1/2003 |
| WO | WO 03/006409 | A1 | 1/2003 |
| WO | WO 03/032967 | A1 | 4/2003 |
| WO | WO 03/062182 | A1 | 7/2003 |

* cited by examiner

*Primary Examiner* — Jon P Weber
*Assistant Examiner* — Satyendra Singh
(74) *Attorney, Agent, or Firm* — Sughrue Mion, PLLC

(57) ABSTRACT

The present invention has its object to provide a method for stabilizing reduced coenzyme $Q_{10}$, which is usable as foods, functional nutritive foods, specific health foods, nutritional supplements, nutrients, animal drugs, drinks, feeds, cosmetics, medicines, remedies, preventive drugs and the like. Reduced coenzyme $Q_{10}$, which is readily oxidized in the air, is stabilized by causing ascorbic acid or a related compound thereof to coexist with a polyglycerol fatty acid ester with a polymerization degree of glycerol being not lower than 3 and/or a condensed ricinoleic acid polyglyceride in a mixture of the reduced coenzyme $Q_{10}$ and an oil and fat.

11 Claims, No Drawings

METHOD FOR STABILIZING REDUCED COENZYME $Q_{10}$

TECHNICAL FIELD

The present invention relates to a method for stabilizing reduced coenzyme $Q_{10}$. Reduced coenzyme $Q_{10}$ shows higher oral absorbability as compared with oxidized coenzyme $Q_{10}$ and is a compound useful as excellent products such as foods, functional nutritive foods, specific health foods, nutritional supplements, nutrients, animal drugs, drinks, feeds, cosmetics, medicines, remedies, preventive drugs and the like.

BACKGROUND ART

It is known that reduced coenzyme $Q_{10}$ can be obtained, for example, by such a method known in the art as synthesis, fermentation or extraction from a natural product, followed by concentration of the reduced coenzyme $Q_{10}$ fraction in the eluent by chromatography (Patent Document 1). It is described in the above-cited patent document that, in this case, oxidized coenzyme $Q_{10}$ contained in the reduced coenzyme $Q_{10}$ may be reduced with an ordinary reducing agent such as sodium borohydride or sodium dithionite (sodium hyposulfite), followed by concentration by chromatography and that reduced coenzyme $Q_{10}$ can also be obtained by the method comprising reacting the above-mentioned reducing agent with the existing high-purity coenzyme $Q_{10}$.

However, it is not always possible to recover the thus-obtained reduced coenzyme $Q_{10}$ in a highly pure condition; rather, it is often obtained in the form of, for example, low-purity crystals or an oily substance or semisolid containing oxidized coenzyme $Q_{10}$ and other impurities.

The present inventors have made intensive investigations and established several methods for obtaining high-quality reduced coenzyme $Q_{10}$, and have applied for patent (e.g. Patent Documents 2 to 4).

However, reduced coenzyme $Q_{10}$ is readily oxidized to oxidized coenzyme $Q_{10}$ by molecular oxygen and even when high-quality reduced coenzyme $Q_{10}$ is produced by such methods as disclosed in the above-cited patent applications, it is still an important problem how to stabilize reduced coenzyme $Q_{10}$ in processing reduced coenzyme $Q_{10}$ into foods, functional nutritive foods, specific health foods, nutritional supplements, nutrients, animal drugs, drinks, feeds, cosmetics, medicines, remedies, preventive drugs and the like or raw materials or compositions therefor and/or storing them after processing. It is very difficult to completely eliminate or shut out oxygen in the above-mentioned processing and storing, and residual oxygen or newcomer oxygen, in particular, exerts great adverse influences during warming in the step of processing and/or during a long period of storage. The above-mentioned oxidation is confronted with a quality problem, namely the formation of oxidized coenzyme $Q_{10}$ as a byproduct.

Thus, it is a very important problem to stabilize (protect against oxidation) reduced coenzyme $Q_{10}$. Since, however, reduced coenzyme $Q_{10}$ is not yet available on the market, few investigations have been made concerning the method for stably maintaining reduced coenzyme $Q_{10}$ or the composition therefor. There are only a few reports describing, for example, a composition comprising a reducing agent caused to coexist and a method for preparing the same (Patent Document 5) and a stabilized composition comprising reduced coenzyme $Q_{10}$ and an oil and fat and/or a polyol (Patent Document 6).

In the above-cited Patent Document 5, the following are disclosed:

1) A composition comprising reduced coenzyme $Q_{10}$, an effective amount of a reducing agent for inhibiting the reduced coenzyme $Q_{10}$ from being oxidized into oxidized coenzyme $Q_{10}$, and an effective amount of a surfactant or a vegetable oil or a mixture of these for dissolving the reduced coenzyme $Q_{10}$) and the reducing agent, if necessary together with a solvent;

2) A composition for oral administration as prepared by making the above composition into gelatin capsules or tablets; and, further, 3) A method for preparing the above composition containing reduced coenzyme $Q_{10}$ produced in situ using oxidized coenzyme $Q_{10}$ and a reducing agent.

However, whereas it describes the preparation method or composition, the above Patent Document 5 does not refer to the quality of reduced coenzyme $Q_{10}$ contained in the composition (for example, the weight ratio of reduced coenzyme $Q_{10}$ to oxidized coenzyme $Q_{10}$) at all. Further, while it describes that reduced coenzyme $Q_{10}$ is stabilized, it contains no detailed description of the stabilizing effects or examples; hence what the extent of stabilization can be expected is not clear. Further, the above-mentioned composition and the method for preparing the same are very complicated and troublesome since the composition is given a plurality of roles (namely, the first role as a field of reaction for reducing oxidized coenzyme $Q_{10}$ to reduced coenzyme $Q_{10}$ and the second role in stably maintaining the reduced coenzyme $Q_{10}$). Furthermore, the reaction mixture as such is used in the above-mentioned composition and the method for preparing the same and, therefore, the composition can hardly be said to be safe. Although the surfactants specifically disclosed in the above Patent Document 5 are Span 80 and Tween 80, the use of Tween 80 and like polyoxyethylenesorbitan fatty acid esters is legally limited in some countries and therefore these substances cannot be used in some cases.

On the other hand, Patent Document 6 describes that reduced coenzyme $Q_{10}$ is stabilized in the presence of an oil and fat or a polyol and that a polyglycerol fatty acid ester, more specifically a polyglycerol fatty acid ester with a polymerization degree being 2, is a surfactant which will not hinder the stabilizing effect of such oil and fat or polyol.

Patent Document 1: Japanese Kokai Publication Hei-10-109933
Patent Document 2: WO03/06408
Patent Document 3: WO03/06409
Patent Document 4: WO03/32967
Patent Document 5: WO01/52822
Patent Document 6: WO03/062182

SUMMARY OF THE INVENTION

Preliminary investigations made by the present inventors concerning the so-far alleged effects of stabilizing reduced coenzyme $Q_{10}$ such as those mentioned above have revealed that the stability of the reduced coenzyme $Q_{10}$-containing composition specifically disclosed in Patent Document 5 is not always satisfactory. Further, while the diglycerol fatty acid ester used in the examples in Patent Document 6 does not interfere with the stabilization, it is currently desired that the reduced coenzyme $Q_{10}$-containing composition is further stabilized according to need in certain fields.

In view of the foregoing, it is an object of the present invention to provide a simple and convenient method for protecting reduced coenzyme $Q_{10}$ against oxidation and stably maintaining the same for a long period of time in processing the same into foods, functional nutritive foods, specific health foods, nutritional supplements, nutrients, animal drugs, drinks, feeds, cosmetics, medicines, remedies, preventive drugs and the like containing reduced coenzyme $Q_{10}$, or into raw materials or compositions therefor and/or in storing them after processing as well as a composition or oral dosage form comprising the same.

The present inventors made intensive investigations in an attempt to accomplish the above object and, as a result, found that when ascorbic acid or a related compound thereof and a specific surfactant are used in an oil and fat for stabilizing reduced coenzyme $Q_{10}$, the reduced coenzyme $Q_{10}$ can be surprisingly ideally protected from oxidation by molecular oxygen and the reduced coenzyme $Q_{10}$ can be stored stably for a long period of time.

Thus, the present invention relates to a method for stabilizing reduced coenzyme $Q_{10}$ which comprises causing ascorbic acid or a related compound thereof to coexist with a polyglycerol fatty acid ester with a polymerization degree of glycerol being not lower than 3 and/or a condensed ricinoleic acid polyglyceride in a mixture of the reduced coenzyme $Q_{10}$ and an oil and fat.

The invention also relates to a stable composition comprising reduced coenzyme $Q_{10}$ which comprises ascorbic acid or a related compound thereof together with the reduced coenzyme $Q_{10}$, an oil and fat, a polyglycerol fatty acid ester with a polymerization degree of glycerol being not lower than 3 and/or a condensed ricinoleic acid polyglyceride.

DETAILED DESCRIPTION OF THE INVENTION

In the following, the invention is described in detail. "Coenzyme $Q_{10}$" merely so referred to herein does not distinguish between the oxidized form and reduced form; when both forms occur in admixture, the term refers to the whole mixture.

According to the stabilization method of the invention, ascorbic acid or a related compound thereof is caused to coexist with a polyglycerol fatty acid ester with a polymerization degree of glycerol being not lower than 3 and/or a condensed ricinoleic acid polyglyceride in a mixture of the reduced coenzyme $Q_{10}$ and an oil and fat, to thereby stabilize the reduced coenzyme $Q_{10}$. The present invention further provides a stable composition comprising reduced coenzyme $Q_{10}$ which comprises ascorbic acid or a related compound thereof as well as the reduced coenzyme $Q_{10}$, an oil and fat, a polyglycerol fatty acid ester with a polymerization degree of glycerol being not lower than 3 and/or a condensed ricinoleic acid polyglyceride.

In the practice of the invention, any polyglycerol fatty acid ester can be used irrespective of the number of fatty acid residues or the species thereof, provided that the polymerization degree of glycerol is not lower than 3. The polyglycerol fatty acid ester is a compound represented by the following general formula (1):

(1)

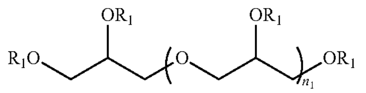

Here, generally, $n_1$ is an integer of not smaller than 0, and $(n_1+1)$ indicates the polymerization degree of glycerol. Thus, in the case of the polyglycerol fatty acid ester to be used in the practice of the invention, $n_1$ is an integer of not smaller than 2. Each $R_1$ independently represents a fatty acid residue (excluding the case of its being a condensed ricinoleic acid-based fatty acid residue) or a hydrogen atom. The case of all $R_1$ moieties each being a hydrogen atom is excluded.

In the practice of the invention, the upper limit to the polymerization degree of glycerol in the polyglycerol fatty acid ester is not particularly restricted but preferably is not higher than 22, more preferably not higher than 15, still more preferably not higher than 10. Thus, the polymerization degree of glycerol in the polyglycerol fatty acid ester is preferably 3 to 22, more preferably 3 to 15, still more preferably 3 to 10, further more preferably 4 to 10.

Various fatty acid residues, either saturated or unsaturated, may be used as the fatty acid residue(s) in the polyglycerol fatty acid ester (in the case of $R_1$ in the above general formula (1) being other than a hydrogen atom), without any particular restriction. Particularly preferred are those fatty acid residues containing 8 to 18 carbon atoms. As such fatty residues, there may be mentioned, for example, those fatty acid residues derived from caprylic acid, capric acid, lauric acid, myristic acid, palmitic acid, stearic acid, isostearic acid, oleic acid, linolic acid and linolenic acid, among others. In cases where there are two or more fatty acid residues, the respective fatty acid residues may be the same or different. From the ready availability and the like viewpoints, they are preferably identical with one another.

The number of fatty acid residues in the polyglycerol fatty acid ester (number of such residues in the case of $R_1$ in the above general formula (1) being a fatty acid residue) varies according to the polymerization degree of glycerol, among others; hence, it is not particularly restricted. The upper limit is the number of hydroxyl groups occurring in the polyglycerol skeleton (i.e. polymerization degree of glycerol+2). Preferred are those polyglycerol fatty acid esters in which the "number of fatty acid residues/(polymerization degree of glycerol+2)" is not higher than 0.7, more preferably the "number of fatty acid residues/(polymerization degree of glycerol+2)" is not higher than 0.5, still more preferably the "number of fatty acid residues/(polymerization degree of glycerol+2)" is not higher than 0.3. Most preferred are polyglycerol mono-fatty acid esters in which the number of fatty acid residues is 1. The number of fatty acid residues in the polyglycerol fatty acid ester is particularly preferably within the range of 1 to 5.

As specific examples of the polyglycerol fatty acid ester which can be used in the practice of the invention, there may be mentioned, among others, triglycerol mono-fatty acid esters, triglycerol di-fatty acid esters, triglycerol tri-fatty acid esters, triglycerol tetra-fatty acid esters, triglycerol penta-fatty acid esters, tetraglycerol mono-fatty acid esters, tetraglycerol di-fatty acid esters, tetraglycerol tri-fatty acid esters, tetraglycerol tetra-fatty acid esters, tetraglycerol penta-fatty acid esters, tetraglycerol hexa-fatty acid esters, pentaglycerol mono-fatty acid esters, pentaglycerol di-fatty acid esters, pentaglycerol tri-fatty acid esters, pentaglycerol tetra-fatty acid esters, pentaglycerol penta-fatty acid esters, pentaglycerol hexa-fatty acid esters, pentaglycerol hepta-fatty acid esters, hexaglycerol mono-fatty acid esters, hexaglycerol di-fatty acid esters, hexaglycerol tri-fatty acid esters, hexaglycerol tetra-fatty acid esters, hexaglycerol penta-fatty acid esters, hexaglycerol hexa-fatty acid esters, hexaglycerol hepta-fatty acid esters, hexaglycerol octa-fatty acid esters, heptaglycerol mono-fatty acid esters, heptaglycerol di-fatty acid esters, heptaglycerol tri-fatty acid esters, heptaglycerol tetra-fatty acid esters, heptaglycerol penta-fatty acid esters, heptaglycerol hexa-fatty acid esters, heptaglycerol hepta-fatty acid esters, heptaglycerol octa-fatty acid esters, heptaglycerol nona-fatty acid esters, octaglycerol mono-fatty acid esters, octaglycerol di-fatty acid esters, octaglycerol tri-fatty acid esters, octaglycerol tetra-fatty acid esters, octaglycerol penta-fatty acid esters, octaglycerol hexa-fatty acid esters, octaglycerol hepta-fatty acid esters, octaglycerol octa-fatty acid esters, octaglycerol nona-fatty acid esters, octaglycerol deca-fatty acid esters, nonaglycerol mono-fatty acid esters, nonaglycerol di-fatty acid esters, nonaglycerol tri-fatty acid esters, nonaglycerol tetra-fatty acid esters, nonaglycerol penta-fatty acid esters, nonaglycerol hexa-fatty acid esters, nonaglycerol hepta-fatty acid esters, nonaglycerol octa-fatty acid esters, nonaglycerol nona-fatty acid esters, nonaglycerol deca-fatty acid esters, nonaglycerol undeca-fatty acid esters, decaglycerol mono-fatty acid esters, decaglycerol di-fatty acid esters, decaglycerol tri-fatty acid esters, decaglycerol tetra-fatty acid esters, decaglycerol penta-fatty acid esters, decaglycerol hexa-fatty acid esters, decaglycerol hepta-fatty acid esters, decaglycerol octa-fatty acid esters, decaglycerol nona-fatty acid esters, decaglycerol deca-fatty acid esters, decaglycerol undeca-fatty acid esters, decaglycerol dodeca-fatty acid esters, etc.

Preferred are triglycerol mono-fatty acid esters, triglycerol di-fatty acid esters, tetraglycerol mono-fatty acid esters, tetraglycerol di-fatty acid esters, tetraglycerol tri-fatty acid esters, pentaglycerol mono-fatty acid esters, pentaglycerol di-fatty acid esters, pentaglycerol tri-fatty acid esters, hexaglycerol mono-fatty acid esters, hexaglycerol di-fatty acid esters, hexaglycerol tri-fatty acid esters, hexaglycerol tetra-fatty acid esters, heptaglycerol mono-fatty acid esters, heptaglycerol di-fatty acid esters, heptaglycerol tri-fatty acid esters, heptaglycerol tetra-fatty acid esters, octaglycerol mono-fatty acid esters, octaglycerol di-fatty acid esters, octaglycerol tri-fatty acid esters, octaglycerol tetra-fatty acid esters, octaglycerol penta-fatty acid esters, nonaglycerol mono-fatty acid esters, nonaglycerol di-fatty acid esters, nonaglycerol tri-fatty acid esters, nonaglycerol tetra-fatty acid esters, nonaglycerol penta-fatty acid esters, decaglycerol mono-fatty acid esters, decaglycerol di-fatty acid esters, decaglycerol tri-fatty acid esters, decaglycerol tetra-fatty acid esters, decaglycerol penta-fatty acid esters, and decaglycerol hexa-fatty acid esters, among others. Particularly preferred are triglycerol mono-fatty acid esters, tetraglycerol mono-fatty acid esters, pentaglycerol mono-fatty acid esters, pentaglycerol di-fatty acid esters, hexaglycerol mono-fatty acid esters, hexaglycerol di-fatty acid esters, heptaglycerol mono-fatty acid esters, heptaglycerol di-fatty acid esters, octaglycerol mono-fatty acid esters, octaglycerol di-fatty acid esters, octaglycerol tri-fatty acid esters, nonaglycerol mono-fatty acid esters, nonaglycerol di-fatty acid esters, nonaglycerol tri-fatty acid esters, decaglycerol mono-fatty acid esters, decaglycerol di-fatty acid esters, and decaglycerol tri-fatty acid esters, among others. Most preferred are triglycerol mono-fatty acid esters, tetraglycerol mono-fatty acid esters, pentaglycerol mono-fatty acid esters, hexaglycerol mono-fatty acid esters, heptaglycerol mono-fatty acid esters, octaglycerol mono-fatty acid esters, nonaglycerol mono-fatty acid esters, and decaglycerol mono-fatty acid ester, among others.

The polymerization degree of glycerol in the condensed ricinoleic acid polyglyceride to be used in the practice of the invention is not particularly restricted. The condensed ricinoleic acid polyglyceride is a compound represented by the following general formula (2):

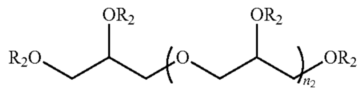
(2)

(In the above formula, $n_2$ is an integer not smaller than 0, $(n_2+1)$ represents the polymerization degree of glycerol; and each $R_2$ independently represents the fatty acid residue of condensed ricinoleic acid represented by the general formula (3) given below (in which m represents an integer of 0 to 18) or a hydrogen atom, excluding the case of all $R_2$ moieties each being a hydrogen atom.)

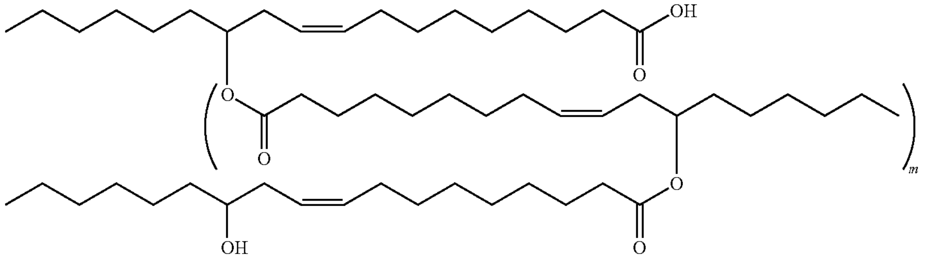
(3)

In the practice of the invention, the polymerization degree of glycerol in the condensed ricinoleic acid polyglyceride ($(n_2+1)$ in the above general formula (2)) is not particularly restricted but may be, for example, 1 to 10. The polymerization degree of glycerol is preferably not lower than 1, more preferably not lower than 2, still more preferably not lower than 3. The upper limit is not particularly restricted but is preferably not higher than 10, more preferably not higher than 8, still more preferably not higher than 6.

As such condensed ricinoleic acid polyglyceride, there may be mentioned, for example, condensed ricinoleic acid monoglyceride, condensed ricinoleic acid diglyceride, condensed ricinoleic acid triglyceride, condensed ricinoleic acid tetraglyceride, condensed ricinoleic acid pentaglyceride, condensed ricinoleic acid hexaglyceride, condensed ricinoleic acid heptaglyceride, condensed ricinoleic acid octaglyceride, condensed ricinoleic acid nonaglyceride and condensed ricinoleic acid decaglyceride, among others. Preferred are condensed ricinoleic acid tetraglyceride and condensed ricinoleic acid hexaglyceride, among others.

While either one component from among the above-mentioned polyglycerol fatty acid ester and condensed ricinoleic acid polyglyceride may be used singly, it is of course possible to use both in combination. In either case, the polyglycerol fatty acid ester itself may comprise one species or two or more species. Similarly, the condensed ricinoleic acid polyglyceride may comprise one species or two or more species.

The oil and fat to be used in the practice of the invention is not particularly restricted but may be a natural oil and fat derived from animals or vegetables, or a synthetic oil and fat or a modified oil and fat. As the vegetable oil and fat, there may be mentioned, for example, coconut oil, palm oil, palm kernel oil, linseed oil, camellia oil, brown rice germ oil, rapeseed oil, rice oil, olive oil, peanut oil, corn oil, wheat germ oil, soybean oil, perilla oil, cotton seed oil, sunflower seed oil, kapok oil, evening primrose oil, shea butter, sal fat, cacao butter, sesame oil and safflower oil, among others. As the animal oil and fat, there may be mentioned, for example, lard, milk fat, fish oil and beef tallow, among others. There may further be mentioned modified oils and fats (e.g. hydrogenated oils) derived from those mentioned above by fractionation, hydrogenation or transesterification, for instance. Medium chain fatty acid triglycerides (MCTs), fatty acid partial glycerides, phospholipids and the like may of course be used. These oils and fats may be used singly or two or more of them may be used in combination.

As the medium chain fatty acid triglycerides, there may be mentioned, for example, those triglycerides in which each fatty acid moiety contains 6 to 12 carbon atoms, preferably 8 to 12 carbon atoms. As the fatty acid partial glycerides, there may be mentioned, for example, those monoglycerides and diglycerides in which each fatty acid moiety contains 6 to 18 carbon atoms, preferably 6 to 12 carbon atoms. As the phospholipids, there may be mentioned lecithin and the like.

Among the oils and fats mentioned above, vegetable oils and fats, synthetic oils and fats and modified oils and fats are preferred from the easy handling, odor and the like viewpoints. An appropriate one is preferably selected from among them taking into consideration the cost of the oils and fats, the stability of reduced coenzyme $Q_{10}$ and the solubility of coenzyme $Q_{10}$, among others. For example, coconut oil, palm oil, palm kernel oil, rapeseed oil, rice oil, olive oil, soybean oil, cotton seed oil, safflower oil, MCTs and the like are preferred, and rice oil, soybean oil, rapeseed oil and MCTs, among others, are particularly preferred. From the viewpoint of solubility of coenzyme $Q_{10}$, MCTs can be used particularly properly.

The weight ratio of the above-mentioned oil and fat to the above-mentioned polyglycerol fatty acid ester and/or condensed ricinoleic acid polyglyceride is not particularly restricted but the lower limit to the weight ratio of oil and fat to the sum (100% by weight) of the oil and fat and the polyglycerol fatty acid ester and/or condensed ricinoleic acid polyglyceride is preferably not lower than about 20% by weight, more preferably not lower than about 30% by weight, still more preferably not lower than about 40% by weight, particularly preferably not lower than about 50% by weight and the upper limit thereto is preferably not higher than about 95% by weight, more preferably not higher than about 90% by weight, still more preferably not higher than about 80% by weight. In other words, that ratio is preferably within the range of about 20 to 95% by weight, more preferably about 30 to 90% by weight, still more preferably about 40 to 80% by weight, particularly preferably about 50 to 80% by weight. In such range, the invention can be practiced in a favorable manner.

In the practice of the invention, reduced coenzyme $Q_{10}$ may comprise reduced coenzyme $Q_{10}$ or a mixture thereof with oxidized coenzyme $Q_{10}$. In the case of such a mixture, the ratio of reduced coenzyme $Q_{10}$ to the total amount of coenzyme $Q_{10}$ (namely the sum of reduced coenzyme $Q_{10}$ and oxidized coenzyme $Q_{10}$) is not particularly restricted but is, for example, not lower than 20% by weight, preferably not lower than 40% by weight, more preferably not lower than 60% by weight, still more preferably not lower than 80%, particularly preferably not lower than 90%, most preferably not lower than 96% by weight. The upper limit thereto is 100%; the upper limit is not particularly restricted but generally is not higher than 99.9% by weight.

The content of reduced coenzyme $Q_{10}$ is not particularly restricted. Generally, considering the stability and ease or convenience of handling of the reduced coenzyme $Q_{10}$ as well, the weight ratio of reduced coenzyme $Q_{10}$ to the sum (100% by weight) of the oil and fat and the polyglycerol fatty acid ester and/or condensed ricinoleic acid polyglyceride is preferably not lower than about 1% by weight, more preferably not lower than about 2% by weight, still more preferably not lower than about 3% by weight, particularly preferably not lower than about 5% by weight, most preferably not lower than about 10% by weight. The upper limit is not particularly restricted but, from the liquid property and the like viewpoints, it is preferably not higher than 50% by weight, more preferably not higher than 30% by weight, still more preferably not higher than 20% by weight.

The ascorbic acid or related compound thereof to be used in the practice of the invention is not particularly restricted but includes not only ascorbic acid but also ascorbic acid analogs such as rhamnoascorbic acid, araboascorbic acid, glucoascorbic acid, fucoascorbic acid, glucoheptoascorbic acid, xyloascorbic acid, galactoascorbic acid, guloascorbic acid, alloascorbic acid, erythroascorbic acid and 6-desoxyascorbic acid. Further, these may be in an ester or salt form. These may be in the L form or D form or in the racemic form. More specifically, there may be mentioned, for example, L-ascorbic acid, L-ascorbyl palmitate, L-ascorbyl stearate, L-ascorbyl dipalmitate, sodium L-ascorbate, calcium L-ascorbate and D-araboascorbic acid. In the practice of the invention, the ascorbic acid and all the related compounds thereof mentioned above can be suitably used. From the ready availability, cost and the like viewpoints, however, L-ascorbic acid, D-araboascorbic acid, L-ascorbyl palmitate and L-ascorbyl stearate, among others, are preferred. It goes without saying that the ascorbic acid and these related compounds thereof may be used singly or a plurality thereof may be used.

The amount of addition of the ascorbic acid or related compound thereof is not particularly restricted provided that an amount thereof effective in stabilizing reduced coenzyme $Q_{10}$ is used. The lower limit thereto is preferably not lower than 1 part by weight, more preferably not lower than about 10 parts by weight, still more preferably not lower than about 20 parts by weight, particularly preferably not lower than about 30 parts by weight, most preferably not lower than about 50 parts by weight, in particular not lower than about 100 parts by weight, per 100 parts by weight of reduced coenzyme $Q_{10}$. The upper limit is not particularly restricted but, from the economical and the like viewpoints, it is preferably not higher than about 10,000 parts by weight, more preferably not higher than about 5,000 parts by weight, still more preferably not higher than about 3,000 parts by weight, particularly preferably not higher than about 2,000 parts by weight.

In the practice of the invention, the oil and fat, polyglycerol fatty acid ester and condensed ricinoleic acid polyglyceride are preferably selected from among those acceptable for food or pharmaceutical use.

In the practice of the present invention, the reduced coenzyme $Q_{10}$ and ascorbic acid or related compound thereof are generally in the form of a solution or suspension in an oil and fat, a polyglycerol fatty acid ester or a condensed ricinoleic acid polyglyceride and, according to the species and the composition ratio of oil and fat, polyglycerol fatty acid ester and/or condensed ricinoleic acid polyglyceride to be used, the composition may take a liquid or solid or slurry form.

In carrying out the method of the invention and in the composition of the invention, the reduced coenzyme $Q_{10}$ and/or ascorbic acid or related compound thereof may be added from an external source. Alternatively, the composition may be one containing the reduced coenzyme $Q_{10}$ produced by reducing oxidized coenzyme $Q_{10}$ with ascorbic acid or a related compound thereof in a composition comprising the above-mentioned oil and fat and polyglycerol fatty acid ester and/or condensed ricinoleic acid polyglyceride. In view of the fact that the components of the composition can be simplified and the preparation thereof is easy and simple and for the purpose of avoiding the risk of the oxidation product (corresponding dehydroascorbic acid or a related compound thereof) generated from the ascorbic acid or related compound thereof used in reducing oxidized coenzyme $Q_{10}$ being converted to hazardous oxalic acid, among others, it is generally desirable that the reduced coenzyme $Q_{10}$ and/or ascorbic acid or related compound thereof is externally added.

Referring to the stabilization method and composition of the invention, the composition simplest in constitution is of course a composition comprising reduced coenzyme $Q_{10}$, ascorbic acid or a related compound thereof, an oil and fat, and a polyglycerol fatty acid ester with a polymerization degree of glycerol being not lower than 3 and/or a condensed ricinoleic acid polyglyceride. It is permissible, however, to add a component substantially incapable of inhibiting the stabilization of reduced coenzyme $Q_{10}$ or add even a component capable of inhibiting the stabilization of reduced coenzyme $Q_{10}$ if in an amount incapable of substantially inhibiting that stabilization, and there will be a number of such components. From such viewpoint, it is the essence of the present invention to provide a composition containing reduced coenzyme $Q_{10}$, ascorbic acid or a related compound thereof, an oil and fat, a polyglycerol fatty acid ester with a polymerization degree of glycerol being not lower than 3, and/or a condensed ricinoleic acid polyglyceride in which composition the stabilization of the reduced coenzyme $Q_{10}$ will not be substantially inhibited; in the practice of the invention, those cases in which other components incapable of substantially inhibiting the stabilization of the reduced coenzyme $Q_{10}$ are contained in the composition are not excluded. As such components, there may be mentioned surfactants other than the polyglycerol fatty acid ester with a polymerization degree of glycerol being not lower than 3, and/or condensed ricinoleic acid polyglyceride, ethanol and water, among others.

As such surfactants, there may be mentioned, for example, organic acid monoglycerides, sucrose fatty acid esters, and polyglycerol fatty acid esters with a polymerization degree of glycerol being 1 or 2.

The organic acid monoglycerides are not particularly restricted but include, for example, acetic acid monoglyceride, lactic acid monoglyceride, citric acid monoglyceride, diacetyltartaric acid monoglyceride and succinic acid monoglyceride.

The sucrose fatty acid esters are not particularly restricted but include, for example, sucrose stearates, sucrose palmitates, sucrose myristates, sucrose oleates, sucrose laurates, sucrose behenates and sucrose ercates. The above-mentioned sucrose fatty acid esters can be used irrespective of whether they are monoesters or polyesters. Of course, they may be mixed fatty acid esters containing a plurality of fatty acid residues.

The polyglycerol fatty acid esters with a polymerization degree of glycerol being 1 or 2 are not particularly restricted but include monoglycerol mono-fatty acid esters, diglycerol mono-fatty acid esters and diglycerol di-fatty acid esters.

When such a surfactant as mentioned above is used, the amount of addition thereof is not particularly restricted but may be properly determined considering the cost and ease of handing, among others. However, the lower limit to the addition amount relative to the total weight (100% by weight) of the composition (including the surfactant above mentioned) is generally not lower than 1% by weight, preferably not lower than 3% by weight, more preferably not lower than 5% by weight, still more preferably not lower than 10% by weight, while the upper limit is generally not higher than 90% by weight, preferably not higher than 70% by weight, more preferably not higher than 60% by weight, still more preferably not higher than 30% by weight, particularly preferably not higher than 20% by weight. Of course, an addition amount beyond the above range may also be used according to need. Of course, it is also possible to use two or more surfactants, without causing any trouble.

It is not prohibited to add other pharmaceutically acceptable components to the composition comprising reduced coenzyme $Q_{10}$, ascorbic acid or a related compound thereof, an oil and fat, a polyglycerol fatty acid ester with a polymerization degree of glycerol being not lower than 3, and/or a condensed ricinoleic acid polyglyceride. Such substances are not particularly restricted but include, for example, an excipient, a disintegrating agent, a lubricant, a binder, an antioxidant, a colorant, an anticoagulant, an absorption promoter, a dissolution aid for an active ingredient, a stabilizer and a viscosity modifier, among others. Of course, it is not prohibited to cause another active ingredient than coenzyme $Q_{10}$ to heighten the added value of the composition.

The excipient is not particularly restricted but includes, for example, white sugar, lactose, glucose, corn starch, mannitol, crystalline cellulose, calcium phosphate and calcium sulfate.

The disintegrating agent is not particularly restricted but includes, for example, starch, agar, calcium citrate, calcium carbonate, sodium hydrogen carbonate, dextrin, crystalline cellulose, carboxymethylcellulose and tragacanth.

The lubricant is not particularly restricted but includes, for example, talc, magnesium stearate, polyethylene glycol, silica and hydrogenated vegetable oils.

The binder is not particularly restricted but includes, for example, ethylcellulose, methylcellulose, hydroxypropylmethylcellulose, tragacanth, shellac, gelatin, gum arabic, polyvinylpyrrolidone, polyvinyl alcohol, polyacrylic acid, polymethacrylic acid and sorbitol.

The antioxidant is not particularly restricted but includes, for example, tocopherol, vitamin A, β-carotene, sodium hydrogen sulfite, sodium thiosulfate, sodium pyrosulfite and citric acid.

The colorant is not particularly restricted but includes, for example, those acceptable as additives for use in drugs and foods.

The anticoagulant is not particularly restricted but includes, for example, stearic acid, talc, light anhydrous silicic acid and hydrous silicon dioxide.

The absorption promoter is not particularly restricted but includes, for example, higher alcohols, higher fatty acids and those surfactants mentioned hereinabove.

The dissolution aid for an active ingredient is not particularly restricted but includes, for example, such organic acids as fumaric acid, succinic acid and malic acid.

The stabilizer is not particularly restricted but includes, for example, benzoic acid, sodium benzoate and ethyl parahydroxybenzoate.

The viscosity modifier is not particularly restricted but includes, for example, beeswax, carnauba wax, candelilla wax, rice bran wax, sugar cane wax, shellac wax and jojoba wax. Preferred are beeswax, carnauba wax and rice bran wax; and, beeswax is particularly preferred.

The above-mentioned active ingredient other than the reduced coenzyme $Q_{10}$ is not particularly restricted but includes, for example, amino acids, vitamins such as vitamin E and derivatives thereof, carotenoides such as β-carotene and astaxanthine, minerals, polyphenols, organic acids, sugars, peptides and proteins.

Although it can be used as such, the above-mentioned composition of the invention can be preferably used in such processed forms for oral administration as capsules (hard capsules, soft capsules), tablets, chewable tablets, syrups and drinks, or in such processed forms as creams, suppositories and toothpastes. Particularly preferred are capsules, in particular soft capsules. The base material for capsules is not particularly restricted but includes, among others, gelatin species derived from bovine bones, bovine skins, pigskins, fish skins, etc. Other base materials (e.g. thickening stabilizers for example seaweed-derived products such as carrageenan and alginic acid, vegetable seed-derived products such as locust bean gum and guar gum, etc., and agents for manufacturing including celluloses), which are usable as food additives, can also be used.

For producing the effects of the invention to the full, the method of the invention is preferably carried out in a deoxygenated atmosphere, for instance, and the composition of the invention is preferably prepared and/or stored in such an atmosphere. The above-mentioned processed forms are also preferably produced and stored after processing in a deoxygenated atmosphere. A deoxygenated atmosphere can be created by substitution with an inert gas, pressure reduction or boiling, or a combination thereof. At least the employment of substitution with an inert gas, namely the use of an inert gas atmosphere, is appropriate. As the inert gas, there may be mentioned, for example, nitrogen gas, helium gas, argon gas, hydrogen gas and carbon dioxide gas, and nitrogen gas is preferred among others.

As described hereinabove, reduced coenzyme $Q_{10}$ can be stored stably by preparing a composition comprising the reduced coenzyme $Q_{10}$, ascorbic acid or related compound thereof, an oil and fat, a polyglycerol fatty acid ester with a polymerization degree of glycerol being not lower than 3 and/or a condensed ricinoleic acid polyglyceride or further processing the composition obtained into such forms as oral dosage forms. The residual reduced coenzyme $Q_{10}$ ratio after the lapse of a certain predetermined period of time is preferably not lower than 80% by weight, more preferably not lower than 90% by weight, still more preferably not lower than 95% by weight.

The "residual ratio" so referred to herein is calculated from the weight ratio (absolute amount (or concentration) of reduced coenzyme $Q_{10}$ in the composition after a predetermined period of storage)/(absolute amount (or concentration) of reduced coenzyme $Q_{10}$ before storage). The predetermined period of storage is, for example, not shorter than 1 day, preferably not shorter than 1 week, more preferably not shorter than 1 month, still more preferably not shorter than half a year, particularly preferably not shorter than 1 year, most preferably not shorter than 2 years.

The term "stabilizing (or "stable composition")" is used herein to mean protection of reduced coenzyme $Q_{10}$ against oxidation to increase the residual ratio thereof as compared with other methods or the storage thereof in other compositions; thus, for example, it is meant by the term that the residual ratio is maintained during the above-mentioned storage period (or the composition can maintain the residual ratio); and the residual reduced coenzyme $Q_{10}$ ratio after 1 month of storage in the air at 40° C. is, for example, preferably not lower than 80% by weight, more preferably not lower than 85% by weight, still more preferably not lower than 90% by weight.

In accordance with the present invention, it is possible to stabilize reduced coenzyme $Q_{10}$ by adequately protecting the same against oxidation. Further, it is possible to provide a composition in which reduced coenzyme $Q_{10}$ can be stored stably; in particular, it is possible to provide a stabilized reduced coenzyme $Q_{10}$-containing composition to be used as a composition for use in foods, drugs and so forth by using safe and easy-to-handle reagents.

BEST MODES FOR CARRYING OUT THE INVENTION

The following examples illustrate the present invention in further detail. These examples are, however, by no means limitative of the scope of the invention.

In the examples, the purity of reduced coenzyme $Q_{10}$ and the weight ratio of reduced coenzyme $Q_{10}$ to oxidized coenzyme $Q_{10}$ were determined by HPLC analysis under the conditions given below. It is to be noted, however, that the purity of the reduced coenzyme $Q_{10}$ obtained does not define any limit value of the purity in the practice of the invention; similarly, the weight ratio of reduced coenzyme $Q_{10}$ to reduced coenzyme $Q_{10}$ plus oxidized coenzyme $Q_{10}$ as found does not define any upper limit value of such weight ratio, either.

(HPLC Analysis Conditions)

Column: SYMMETRY C18 (product of Waters Corporation), 250 mm (length), 4.6 mm (inside diameter); mobile phase: $C_2H_5OH:CH_3OH=4:3$ (v:v); detection wavelength: 210 nm; flow rate: 1 ml/min; retention time of reduced coenzyme $Q_{10}$: 9.1 min; retention time of oxidized coenzyme $Q_{10}$: 13.3 min.

Production Example 1

Oxidized coenzyme $Q_{10}$ (purity 99.4%; 100 g) and 60 g of L-ascorbic acid were added to 1,000 g of ethanol, and the reduction reaction was carried out with stirring at 78° C. After 30 hours, the reaction mixture was cooled to 50° C., and 400 g of ethanol was added while the same temperature was maintained. This ethanol solution (containing 100 g of reduced coenzyme $Q_{10}$) was cooled to 2° C. at a cooling rate of 10° C./hour with stirring to give a white slurry. The slurry obtained was filtered under reduced pressure, the wet crystal was washed in sequence with cold ethanol, cold water and cold ethanol (the temperature of the cold solvents used for washing: 2° C.), and the wet crystal was further dried under reduced pressure (20 to 40° C., 1 to 30 mmHg) to give 95 g of white dry crystal (yield of isolated product: 95 mole %). All the operations except for vacuum drying were carried out in a nitrogen atmosphere. The weight ratio of reduced coenzyme $Q_{10}$ to oxidized coenzyme $Q_{10}$ in the crystal obtained was 99.5/0.5, and the purity of reduced coenzyme $Q_{10}$ was 99.2%.

Example 1 And Comparative Example 1

0.3 g of the crystal of reduced coenzyme $Q_{10}$ as obtained in Production Example 1 and 0.3 g of L-ascorbyl palmitate were added to 10 g of each of the mixtures of the surfactant, and oil and fat specified in Table 1 (weight ratio of surfactant to oil and fat: 3/7), and the resulting mixture was stored in the air at 40° C. The weight ratios of reduced coenzyme $Q_{10}$ to oxidized coenzyme $Q_{10}$ after the lapse of 1 month were as shown in Table 1.

TABLE 1

| Surfactant | Oil/fat | R |
|---|---|---|
| (Example 1) | | |
| Triglycerol monooleate | MCT | 93.9/6.1 |
| Tetraglycerol monooleate | MCT | 95.1/4.9 |
| Hexaglycerol monooleate | MCT | 98.4/1.6 |
| Hexaglycerol monooleate | Rapeseed oil | 98.2/1.8 |
| Decaglycerol monooleate | MCT | 98.6/1.4 |
| Decaglycerol monooleate | Rapeseed oil | 98.2/1.8 |
| Decaglycerol pentaoleate | MCT | 93.1/6.9 |
| Condensed ricinoleic acid tetraglyceride | MCT | 98.1/1.9 |
| Condensed ricinoleic acid hexaglyceride | MCT | 98.5/1.5 |
| (Comparative Example 1) | | |
| Diglycerol monooleate | MCT | 70.2/29.8 |

R: weight ratio of reduced coenzyme $Q_{10}$ to oxidized coenzyme $Q_{10}$

From the above results, it was found that, in the case of polyglycerol fatty acid esters, the polymerization degree of glycerol significantly influences the stability of reduced coenzyme $Q_{10}$ and, when polyglycerol fatty acid esters with a polymerization degree of glycerol being not lower than 3 or condensed ricinoleic acid polyglycerides are used, they produce marked stabilizing effects.

Example 2

Mixture preparation and storage were carried out in quite the same manner as in Example 1 except that L-ascorbic acid was used in lieu of L-ascorbyl palmitate and that the surfactants and oils and fats specified in Table 2 were used. The weight ratios of reduced coenzyme $Q_{10}$ to oxidized coenzyme $Q_{10}$ after the lapse of 1 month were as shown in Table 2.

TABLE 2

| Surfactant | Oil/fat | R |
|---|---|---|
| Triglycerol monooleate | MCT | 94.9/5.1 |
| Tetraglycerol monooleate | MCT | 96.4/3.6 |
| Hexaglycerol monooleate | MCT | 95.9/4.1 |
| Hexaglycerol monooleate | Rapeseed oil | 95.1/4.9 |
| Decaglycerol monooleate | MCT | 97.1/2.9 |
| Decaglycerol monooleate | Rapeseed oil | 96.8/3.2 |
| Decaglycerol pentaoleate | MCT | 97.0/3.0 |

R: weight ratio of reduced coenzyme $Q_{10}$ to oxidized coenzyme $Q_{10}$

Comparative Example 2

Mixture preparation and storage were carried out in quite the same manner as in Example 1 except that L-ascorbyl palmitate was not added and that the surfactants and oils and fats specified in Table 3 were used. The weight ratios of reduced coenzyme $Q_{10}$ to oxidized coenzyme $Q_{10}$ after the lapse of 5 days were as shown in Table 3.

TABLE 3

| Surfactant | Oil/fat | R |
|---|---|---|
| Triglycerol monooleate | MCT | 49.3/50.7 |
| Tetraglycerol monooleate | MCT | 48.3/51.7 |

TABLE 3-continued

| Surfactant | Oil/fat | R |
|---|---|---|
| Hexaglycerol monooleate | MCT | 68.2/31.8 |
| Hexaglycerol monooleate | Rapeseed oil | 59.3/40.7 |
| Decaglycerol monooleate | MCT | 65.0/35.0 |
| Decaglycerol monooleate | Rapeseed oil | 59.1/40.9 |
| Decaglycerol pentaoleate | MCT | 53.3/46.7 |
| Condensed ricinoleic acid tetraglyceride | MCT | 33.3/66.7 |
| Condensed ricinoleic acid hexaglyceride | MCT | 43.2/56.8 |

R: weight ratio of reduced coenzyme $Q_{10}$ to oxidized coenzyme $Q_{10}$

Example 3

0.3 g of the crystals of reduced coenzyme $Q_{10}$ as obtained in Production Example 1 and 0.3 g of L-ascorbyl palmitate were added to 10 g of each of the mixtures of the surfactant and oil and fat specified in Table 4 (weight ratio of surfactant to oil and fat: 3/7), and the resulting mixture was stored in the air at 60° C. The weight ratios of reduced coenzyme $Q_{10}$ to oxidized coenzyme $Q_{10}$ after the lapse of 6 weeks were as shown in Table 4.

TABLE 4

| Surfactant | Oil/fat | R |
|---|---|---|
| Tetraglycerol monooleate | MCT | 90.3/9.7 |
| Hexaglycerol monooleate | MCT | 91.5/8.5 |
| Hexaglycerol monooleate | Rapeseed oil | 90.7/9.3 |
| Decaglycerol monooleate | MCT | 95.9/4.1 |
| Decaglycerol monooleate | Rapeseed oil | 93.8/6.2 |
| Decaglycerol pentaoleate | MCT | 86.2/13.8 |
| Condensed ricinoleic acid tetraglyceride | MCT | 98.8/1.2 |
| Condensed ricinoleic acid hexaglyceride | MCT | 97.9/2.1 |

R: weight ratio of reduced coenzyme $Q_{10}$ to oxidized coenzyme $Q_{10}$

Comparative Example 3

0.3 g of the crystals of reduced coenzyme $Q_{10}$ as obtained in Production Example 1 and 0.3 g of L-ascorbyl palmitate were added to a mixture composed of 0.5 g of Span 80, 5.5 g of Tween 80, 3.5 g of MCT and 0.5 g of glycerol, and the resulting mixture was stored under the quite the same conditions as in Example 3. The weight ratio of reduced coenzyme $Q_{10}$ to oxidized coenzyme $Q_{10}$ after the lapse of 6 weeks was 36.9/63.1.

Example 4

1 g of the crystals of reduced coenzyme $Q_{10}$ as obtained in Production Example 1 and 1 g of L-ascorbyl palmitate were added to 10 g of each of mixtures of hexaglycerol monooleate and MCT in varied weight ratios as shown in Table 5. The resulting mixtures were each stored in the air at 40° C. The weight ratios of reduced coenzyme $Q_{10}$ to oxidized coenzyme $Q_{10}$ after the lapse of 1 month were as shown in Table 5.

TABLE 5

| Hexaglycerol monooleate/MCT weight ratio | R |
|---|---|
| 30/70 | 98.4/1.6 |
| 50/50 | 99.2/0.8 |
| 70/30 | 98.9/1.1 |

R: weight ratio of reduced coenzyme $Q_{10}$ to oxidized coenzyme $Q_{10}$

Dosage Form Example 1

Gelatin soft capsules according to the formulation given below were obtained in the conventional manner by adding the crystals of reduced coenzyme $Q_{10}$ as obtained in Production Example 1 and L-ascorbyl palmitate to a mixture of medium chain fatty acid triglyceride, tetraglycerol monooleate, hydrogenated oil, beeswax and lecithin at 50° C.

| | |
|---|---|
| Reduced coenzyme $Q_{10}$ | 100 weight parts |
| L-Ascorbyl palmitate | 100 weight parts |
| Tetraglycerol monooleate | 320 weight parts |
| Medium chain fatty acid triglyceride | 350 weight parts |
| Hydrogenated oil | 60 weight parts |
| Beeswax | 50 weight parts |
| Lecithin | 20 weight parts |

Dosage Form Example 2

Gelatin soft capsules according to the formulation given below were obtained in the conventional manner by adding the crystals of reduced coenzyme $Q_{10}$ as obtained in Production Example 1 and L-ascorbyl palmitate to a mixture of rapeseed oil, hexaglycerol monooleate, hydrogenated oil, beeswax and lecithin at 50° C.

| | |
|---|---|
| Reduced coenzyme $Q_{10}$ | 100 weight parts |
| L-Ascorbyl palmitate | 100 weight parts |
| Hexaglycerol monooleate | 220 weight parts |
| Rapeseed oil | 450 weight parts |
| Hydrogenated oil | 60 weight parts |
| Beeswax | 50 weight parts |
| Lecithin | 20 weight parts |

Dosage Form Example 3

Gelatin soft capsules according to the formulation given below were obtained in the conventional manner by adding the crystals of reduced coenzyme $Q_{10}$ as obtained in Production Example 1 and L-ascorbyl palmitate to a mixture of medium chain fatty acid triglyceride, decaglycerol monooleate, hydrogenated oil, beeswax and lecithin at 50° C.

| | |
|---|---|
| Reduced coenzyme $Q_{10}$ | 100 weight parts |
| L-Ascorbyl palmitate | 100 weight parts |
| Decaglycerol monooleate | 200 weight parts |
| Medium chain fatty acid triglyceride | 470 weight parts |
| Hydrogenated oil | 60 weight parts |
| Beeswax | 50 weight parts |
| Lecithin | 20 weight parts |

Dosage Form Example 4

Gelatin soft capsules according to the formulation given below were obtained in the conventional manner by adding the crystals of reduced coenzyme $Q_{10}$ as obtained in Production Example 1 and L-ascorbyl palmitate to a mixture of medium chain fatty acid triglyceride, decaglycerol pentaoleate, hydrogenated oil, beeswax and lecithin at 50° C.

| | |
|---|---|
| Reduced coenzyme $Q_{10}$ | 100 weight parts |
| L-Ascorbyl palmitate | 100 weight parts |
| Decaglycerol pentaoleate | 320 weight parts |
| Medium chain fatty acid triglyceride | 350 weight parts |
| Hydrogenated oil | 60 weight parts |
| Beeswax | 50 weight parts |
| Lecithin | 20 weight parts |

Dosage Form Example 5

Gelatin soft capsules according to the formulation given below were obtained in the conventional manner by adding the crystals of reduced coenzyme $Q_{10}$ as obtained in Production Example 1 and L-ascorbic acid to a mixture of medium chain fatty acid triglyceride, hexaglycerol monooleate, hydrogenated oil, beeswax and lecithin at 50° C.

| | |
|---|---|
| Reduced coenzyme $Q_{10}$ | 100 weight parts |
| L-Ascorbic acid | 100 weight parts |
| Hexaglycerol monooleate | 220 weight parts |
| Medium chain fatty acid triglyceride | 450 weight parts |
| Hydrogenated oil | 60 weight parts |
| Beeswax | 50 weight parts |
| Lecithin | 20 weight parts |

Dosage Form Example 6

Gelatin soft capsules according to the formulation given below were obtained in the conventional manner by adding the crystals of reduced coenzyme $Q_{10}$ as obtained in Production Example 1 and L-ascorbic acid to a mixture of medium chain fatty acid triglyceride, condensed ricinoleic acid hexaglyceride, hydrogenated oil, beeswax and lecithin at 50° C.

| | |
|---|---|
| Reduced coenzyme $Q_{10}$ | 100 weight parts |
| L-Ascorbic acid | 100 weight parts |
| Condensed ricinoleic acid hexaglyceride | 200 weight parts |
| Medium chain fatty acid triglyceride | 470 weight parts |
| Hydrogenated oil | 60 weight parts |
| Beeswax | 50 weight parts |
| Lecithin | 20 weight parts |

INDUSTRIAL APPLICABILITY

In accordance with the invention, reduced coenzyme $Q_{10}$ can be properly protected against oxidation and thus stabilized. Further, a composition in which reduced coenzyme $Q_{10}$ can be stored stably can be provided and, in particular, a reduced coenzyme $Q_{10}$-containing composition which can be used as a composition for use as a food or pharmaceutical can be provided by using safe and easy-to-handle reagents.

The invention claimed is:

1. A method for stabilizing reduced coenzyme Q10 which comprises causing ascorbic acid or a related compound thereof to coexist with a polyglycerol oleic acid ester with a polymerization degree of glycerol being not lower than 3 and/or a condensed ricinoleic acid polyglyceride with a degree of polymerization of glycerol of 4 to 6 in a mixture of the reduced coenzyme Q10 and an oil and fat, wherein the ascorbic acid or a related compound thereof is L-ascorbic acid and/or L-ascorbyl palmitate, the number of oleic acid residues in the polyglycerol oleic acid ester is 1 to 5, the weight ratio of the oil and fat to the sum of the oil and fat and the polyglycerol oleic acid ester and/or condensed ricinoleic acid polyglyceride is 20 to 95%, the weight ratio of the reduced coenzyme Q10 to the sum of the oil and fat and the polyglycerol oleic acid ester and/or condensed ricinoleic acid polyglyceride is 1 to 50%, and a residual reduced coenzyme Q10 ratio after 1 month of storage in the air at 40° C. is not lower than 80% by weight.

2. The method for stabilizing reduced coenzyme Q10 according to claim 1 wherein the oil and fat are at least one species selected from the group consisting of coconut oil, palm oil, palm kernel oil, linseed oil, camellia oil, brown rice germ oil, rapeseed oil, rice oil, olive oil, peanut oil, corn oil, wheat germ oil, soybean oil, perilla oil, cotton seed oil, sunflower seed oil, kapok oil, evening primrose oil, shea butter, sal fat, cacao butter, sesame oil, safflower oil, lard, milk fat, fish oil, beef tallow, modified oils and fats derived from these by fractionation, hydrogenation or transesterification, medium chain fatty acid triglycerides, fatty acid partial glycerides and phospholipids.

3. The method for stabilizing reduced coenzyme Q10 according to claim 1 wherein the polymerization degree of glycerol in the polyglycerol oleic acid ester is 3, 4, 6 or 10.

4. The method for stabilizing reduced coenzyme $Q_{10}$ according to claim 1 wherein an amount of the ascorbic acid or related compound thereof is not lower than 10 parts by weight per 100 parts by weight of reduced coenzyme $Q_{10}$.

5. The method for stabilizing reduced coenzyme $Q_{10}$ according to claim 1 which further comprises adding an active ingredient other than reduced coenzyme $Q_{10}$.

6. The method for stabilizing reduced coenzyme $Q_{10}$ according to claim 1 wherein the reduced coenzyme $Q_{10}$ and/or ascorbic acid or related compound thereof is added from an external source.

7. The method for stabilizing reduced coenzyme $Q_{10}$ according to claim 1 which is carried out in a deoxygenated atmosphere.

8. The method for stabilizing reduced coenzyme Q10 according to claim 1 wherein the oil and fat, polyglycerol oleic acid ester and condensed ricinoleic acid polyglyceride are acceptable for food or pharmaceutical use.

9. The method for stabilizing reduced coenzyme $Q_{10}$ according to claim 5 wherein the active ingredient other than reduced coenzyme $Q_{10}$ is at least one species selected from the group consisting of amino acids, vitamins, carotenoides, minerals, polyphenols, organic acids, sugars, peptides and proteins.

10. The method for stabilizing reduced coenzyme $Q_{10}$ according to claim 1 wherein the residual reduced coenzyme $Q_{10}$ ratio after 1 month of storage in the air at 40° C. is not lower than 90% by weight.

11. The method for stabilizing reduced coenzyme $Q_{10}$ according to claim 1 wherein the residual reduced coenzyme $Q_{10}$ ratio is a residual reduced coenzyme $Q_{10}$ ratio after 6 weeks of storage in the air at 60° C. is not lower than 86% by weight.

* * * * *